(12) United States Patent
Wall et al.

(10) Patent No.: US 9,737,204 B2
(45) Date of Patent: Aug. 22, 2017

(54) RETINAL IMAGING APPARATUS AND METHOD

(75) Inventors: Robert Wall, Fife (GB); Derek Swan, Fife (GB); Dan Gray, Fife (GB)

(73) Assignee: OPTOS PLC, Dunfermline, Fife (GB)

( * ) Notice: Subject to any disclaimer, the term of this patent is extended or adjusted under 35 U.S.C. 154(b) by 0 days.

(21) Appl. No.: 13/805,595

(22) PCT Filed: Jun. 2, 2011

(86) PCT No.: PCT/GB2011/051039
§ 371 (c)(1),
(2), (4) Date: Feb. 4, 2013

(87) PCT Pub. No.: WO2012/001383
PCT Pub. Date: Jan. 5, 2012

(65) Prior Publication Data
US 2013/0128224 A1   May 23, 2013

(30) Foreign Application Priority Data

Jul. 1, 2010 (GB) .................................. 1011094.8

(51) Int. Cl.
*A61B 3/00* (2006.01)
*A61B 3/12* (2006.01)
(Continued)

(52) U.S. Cl.
CPC .............. *A61B 3/0008* (2013.01); *A61B 3/12* (2013.01); *A61B 3/14* (2013.01); *G02B 6/0006* (2013.01)

(58) Field of Classification Search
CPC ....... A61B 3/0008; A61B 3/12; A61B 3/1225; A61B 3/102; A61B 3/14
(Continued)

(56) References Cited

U.S. PATENT DOCUMENTS 3,944,341 A * 3/1976 Pomerantzeff ................ 351/206
4,666,269 A   5/1987 Nakamura et al.
(Continued)

FOREIGN PATENT DOCUMENTS

CN   101489468 A   7/2009
EP      615721 A1   9/1994
(Continued)

OTHER PUBLICATIONS

Notification of Reasons for Refusal issued in corresponding Japanese application No. 2013-517526 dated Jun. 2, 2015.
(Continued)

*Primary Examiner* — Zachary Wilkes
(74) *Attorney, Agent, or Firm* — Pavan Agarwal; Shabbi S. Khan; Foley & Lardner LLP

(57) ABSTRACT

The invention provides an apparatus and method for illuminating, imaging and treating the retina of an eye. The apparatus (10) comprises at least one light source (16), wherein the at least one light source (16) is adapted to provide collimated light (20) from a plurality of point sources (22), and wherein each point source (22) lies on an arc (18), and wherein the at least one light source (16) is configured to direct collimated light (20) from each point source (22) along the radius (24) of the arc (18) towards a center point (26) of the arc (18), and wherein, in use, the apparatus (10) is arranged such that the center point (26) of the arc (18) is substantially coincident with the pupillary point (40) of the eye (14), such that collimated light (20) is transmitted from the point source (22) through the pupillary point (40) of the eye (14) to illuminate the retina (12).

20 Claims, 2 Drawing Sheets

(51) Int. Cl.
  *A61B 3/14*      (2006.01)
  *F21V 8/00*      (2006.01)

(58) Field of Classification Search
  USPC .......................................................... 351/221
  See application file for complete search history.

(56) References Cited

U.S. PATENT DOCUMENTS

| | | | |
|---|---|---|---|
| 4,699,482 A * | 10/1987 | Utsugi ........................... | 351/206 |
| 5,585,873 A | 12/1996 | Shalon et al. | |
| 5,815,242 A | 9/1998 | Anderson et al. | |
| 5,835,190 A * | 11/1998 | Miyake ........................... | 351/212 |
| 6,337,920 B1 * | 1/2002 | Muhlhoff ........................ | 382/128 |
| 6,409,346 B1 | 6/2002 | Koest et al. | |
| 7,134,754 B2 * | 11/2006 | Kerr et al. ...................... | 351/206 |
| 7,909,465 B2 * | 3/2011 | Ho et al. ......................... | 351/221 |
| 2004/0156016 A1 | 8/2004 | Kerr et al. | |
| 2007/0024965 A1 | 2/2007 | Sander | |
| 2008/0151185 A1 | 6/2008 | Saito | |
| 2009/0009715 A1 | 1/2009 | Mensink | |

FOREIGN PATENT DOCUMENTS

| | | | |
|---|---|---|---|
| EP | 1933187 A1 | 6/2008 | |
| GB | 2440163 A | 1/2008 | |
| JP | H04-505061 A | 9/1992 | |
| JP | H06-061862 A | 9/1994 | |
| JP | H09-131322 | 5/1997 | |
| JP | 2008-145701 A | 6/2008 | |
| WO | WO99/20174 A1 | 4/1999 | |
| WO | WO99/27844 A1 | 6/1999 | |
| WO | WO02/058590 A3 | 8/2002 | |
| WO | WO 2008116270 A1 * | 10/2008 | ............ A61B 3/103 |

OTHER PUBLICATIONS

Chinese Office Action issued in CN 201180032861.2 dated Jan. 19, 2016.

EP Examination Report issued in EP Application No. 11 727 747.5 dated Nov. 28, 2016.

* cited by examiner

RETINAL IMAGING APPARATUS AND METHOD

The present invention relates to an apparatus and method for illuminating, imaging and treating the retina of a human eye.

Imaging systems, such as scanning laser ophthalmoscopes (SLOs), may comprise a large number of optical components, such as laser scanning elements, scan transfer mirrors, laser sources and detectors. The laser scanning arrangement consists of first and second orthogonal scanning elements, which typically include a high speed rotating polygonal mirror and a motor driven slow speed mirror. These elements are used to create a raster scan pattern of the human retina. The polygon mirror has a plurality of facets and typically provides the vertical scanning of the laser beam, and the slow speed mirror typically provides the horizontal scanning of the laser beam. The scan transfer mirror transfers the two dimensional laser scan pattern created by the scanning elements to the retina of the eye.

While such imaging systems provide acceptable images of the retina of the eye, they are limited in that they are expensive to manufacture (the laser scanning elements and scan transfer mirror are particularly expensive components), large in size and, due to the large number of optical components, have low optical efficiency.

According to a first aspect of the present invention there is provided an apparatus for illuminating the retina of an eye comprising:
  at least one light source,
  wherein the at least one light source is adapted to provide collimated light from a plurality of point sources,
  and wherein each point source lies on an arc,
  and wherein the at least one light source is configured to direct collimated light from each point source along the radius of the arc towards a centre point of the arc,
  and wherein, in use, the apparatus is arranged such that the centre point of the arc is substantially coincident with the pupillary point of the eye, such that collimated light is transmitted from the point source through the pupillary point of the eye to illuminate the retina.

The apparatus may comprise a plurality of light sources, wherein each light source is adapted to provide collimated light from each point source.

The centre of the arc may be coincident with the first nodal point of the eye.

The plurality of collimated light point sources may be arranged in an array such that each point source is equidistant from its adjacent point source. Alternatively, the collimated light point sources may be arranged such that they adjoin one another along the arc.

The radius of the arc may be between 3 mm and 500 mm. Preferably, the radius of the arc may be between 5 mm and 200 mm. More preferably, the radius of the arc is 25 mm.

The apparatus may comprise between 1 and 16,000,000 light sources. Preferably, the apparatus comprises between 100 and 16,000,000 light sources. More preferably, the apparatus comprises 4000 light sources.

The light sources may include a laser, a light emitting diode (LED), a Vertical Cavity Surface Emitting Laser (VCSEL), a super luminescent diode, a diode laser or a collimated incandescent lamp.

Each light source may be adapted to provide light at a wavelength between 450 nm and 1000 nm. Preferably, each light source may be adapted to provide light at a wavelength between 488 nm and 700 nm. More preferably, each light source provides light at a wavelength between 515 nm and 650 nm.

Each light source may be adapted to provide light at a power of between 500 nW and 1 W.

Each light source may include one or more light sources of differing wavelengths.

Each light source may be configured such that the wavelength of light provided is variable.

Each light source may be configured such that the power of light provided is variable.

Each light source may be positioned at or adjacent the point source.

Each light source may include a collimating lens to provide the collimated light from the point source.

Each light source may be positioned remotely from the point source. In this arrangement light is transferred from each light source to the point source via a light transfer device, such as a light guide, optical fibre, or the like. In this arrangement each light source may include a first collimating lens provided at an input to the light transfer device to provide collimated light to the input to the light transfer device and a second collimating lens provided at the output of the light transfer device to provide collimated light at the point source.

Each light source may include a power monitor to monitor the power of the light source.

Each light source may include a polarising element, such as a linear polariser or waveplate.

The apparatus may be configured such that each light source is independently operable. The apparatus may be configured such that each light source is operated sequentially.

The apparatus may be configured such that the operation of each light source is automated. The operation of each light source may be computer-controlled.

The apparatus may be rotatable about an axis which substantially lies on a plane defined by the plurality of point sources and the centre point of the arc. In this arrangement the apparatus may be used to illuminate the surface of the retina, as opposed to a line on the retina. That is, without rotation the apparatus illuminates a line on the retina and with rotation the apparatus illuminates the surface of the retina.

The axis of rotation of the apparatus may be located around the pupillary point of the eye. The axis of rotation of the apparatus may be coincident with the pupillary point of the eye.

The apparatus may be configured such that its rotation about the axis is automated. The rotation of the apparatus may be computer-controlled.

The apparatus may comprise a plurality of collimated point sources lying on a plurality of concentrically aligned arcs. Each arc may have the same radius and centre point. In this arrangement collimated light from each point source is directed radially inwardly along the radius of each arc towards the centre point. In use, the apparatus is arranged such that the centre point is substantially coincident with the pupillary point of the eye, such that collimated light is transmitted from each point source through the pupillary point of the eye to illuminate the retina. The effect of this arrangement is that the apparatus provides a two-dimensional semi-spherical illuminating surface for directing collimated light from each point source through the centre point and to the retina of the eye.

The apparatus may be pivotable between a first position, in which the apparatus may be used to illuminate the first retina of a first eye, and a second position, in which the apparatus may be used to illuminate the second retina of a second eye.

The apparatus may further comprise a light detector for detecting light reflected from the retina to produce an image of the retina. In this arrangement the apparatus illuminates the retina and obtains an image of the illuminated part of the retina. This image is a one-dimensional image. When the apparatus is rotated about the axis described above, a plurality of one-dimensional images of the retina may be obtained and combined to obtain a two-dimensional image of the retina.

Each light source may include a light detector for detecting light reflected from the retina to produce an image of the retina.

The light detector(s) may include fast photo detectors, such as avalanche photo diodes (APDs), PIN diodes, photomultiplier tubes (PMTs), silicon photo multipliers (SPMs), or similar single point detectors.

The light detectors may be located with the light sources.

The apparatus may be configured such that the operation of each light detector is automated. The operation of each light detector may be computer-controlled. The operation of each light detector is synchronised with each light source.

Each detector may include a lens which focuses the reflected collimated light from the retina to the detector. The detector is preferably a point detector and the lens focuses the reflected collimated light to a point on the point detector.

The apparatus may include a single lens which functions as the collimating lens of each light source and the focussing lens of each detector.

The apparatus may include a beam splitter positioned between each light source and each detector. In this arrangement the beam splitter reflects a portion of the light from the light source to the collimating lens. The remaining portion of the light from the light source is transmitted through the beam splitter and towards the power monitor. The majority of the reflected collimated light from the retina is transmitted through the beam splitter to the detector.

The apparatus may further comprise one or more data processing devices for displaying, storing and/or combining the obtained images of the retina.

According to a second aspect of the present invention, there is provided a system for illuminating the retina of each eye of a patient comprising two apparatuses according to the first aspect of the present invention, wherein each apparatus may be capable of illuminating the retina of one eye.

According to a third aspect of the present invention there is provided a method of illuminating the retina of an eye comprising the steps of:
   providing at least one light source, wherein the at least one light source is adapted to provide collimated light from a plurality of point sources;
   arranging each point source on an arc;
   arranging the apparatus such that the centre point of the arc is substantially coincident with the pupillary point of the eye; and
   using the at least one light source to direct collimated light from each point source along the radius of the arc towards the centre point of the arc, such that collimated light is transmitted from the point source through the pupillary point of the eye to illuminate the retina.

The apparatus may comprise a plurality of light sources, wherein each light source is adapted to provide collimated light from each point source.

Each light source may be configured such that the wavelength of light provided is variable and the method may include the further step of varying the wavelength of light from the source.

Each light source may be configured such that the power of light provided is variable and the method may include the further step of varying the power of light from the source.

Each light source may be independently operable and the method may include the further step of operating each light source sequentially.

The operation of each light source may be automated. The operation of each light source may be computer-controlled.

The apparatus may be rotatable about an axis which substantially lies on a plane defined by the plurality of point sources and the centre point of the arc and the method may include the further step of rotating the apparatus about the axis to illuminate the surface of the retina. The axis of rotation of the apparatus may be located around the pupillary point of the eye. The axis of rotation of the apparatus may be coincident with the pupillary point of the eye.

The rotation of the apparatus may be configured such that its rotation about the axis is automated. The rotation of the apparatus may be computer-controlled.

The method may comprise the further step of providing a light detector and using the light detector to detect light reflected from the retina to produce an image of the retina. In this arrangement the method performs the steps of illuminating the retina and obtaining an image of the illuminated retina. Without rotation of the apparatus the image obtained is a one-dimensional image, with rotation of the apparatus the image obtained is a two-dimensional image. The two-dimensional image may be obtained by combining a plurality of one-dimensional images together. The operation of each light detector may be automated. The operation of each light detector may be computer-controlled.

According to a fourth aspect of the present invention there is provided an apparatus for imaging the retina of an eye comprising:
   at least one light source and a plurality of light detectors,
   wherein the at least one light source is adapted to provide collimated light from a plurality of point sources and each light detector is adapted to detect light reflected from the retina,
   and wherein each point source lies on an arc,
   and wherein the at least one light source is configured to direct collimated light from each point source along the radius of the arc towards a centre point of the arc,
   and wherein, in use, the apparatus is arranged such that the centre point of the arc is substantially coincident with the pupillary point of the eye, such that collimated light is transmitted from the point source through the pupillary point of the eye to illuminate the retina and reflected back to the light detector to produce an image of the retina.

The apparatus may comprise a plurality of light sources, wherein each light source is adapted to provide collimated light from each point source.

According to a fifth aspect of the present invention there is provided an apparatus for treating the retina of an eye with collimated light comprising:
   at least one light source,
   wherein the at least one light source is adapted to provide collimated light from a plurality of point sources,
   and wherein each point source lies on an arc,
   and wherein the at least one light source is configured to direct collimated light from each point source along the radius of the arc towards a centre point of the arc, and wherein, in use, the apparatus is arranged such that the centre point of the arc is substantially coincident with the pupillary point of the eye, such that collimated light is transmitted from the point source through the pupillary point of the eye to the retina.

Treatment of the retina is interpreted here to include photodynamic therapy, photo-ablation, photoporation, photoactivation or other methods where the interaction of the light is used to alter the state or structure of the retina or to alter the state of chemicals within the retinal structure.

According to a sixth aspect of the present invention there is provided a method of imaging the retina of an eye comprising the steps of:
providing at least one light source, wherein the at least one light source is adapted to provide collimated light from a plurality of point sources;
providing a plurality of light detectors, wherein each light detector is adapted to detect light reflected from the retina;
arranging each point source on an arc;
arranging the apparatus such that the centre point of the arc is substantially coincident with the pupillary point of the eye; and
using the at least one light source to direct collimated light from each point source along the radius of the arc towards the centre point of the arc, such that collimated light is transmitted from the point source through the pupillary point of the eye to illuminate the retina; and
using each light detector to detect light reflected from the retina to produce an image of the retina.

According to a seventh aspect of the present invention there is provided a method of treating the retina of an eye with collimated light comprising the steps of:
providing at least one light source, wherein the at least one light source is adapted to provide collimated light from a plurality of point sources;
arranging each point source on an arc;
arranging the apparatus such that the centre point of the arc is substantially coincident with the pupillary point of the eye; and
using the at least one light source to direct collimated light from each point source along the radius of the arc towards the centre point of the arc, such that collimated light is transmitted from the point source through the pupillary point of the eye to the retina.

Treatment of the retina is interpreted here to include photodynamic therapy, photo-ablation, photoporation, photoactivation or other methods where the interaction of the light is used to alter the state or structure of the retina or to alter the state of chemicals within the retinal structure.

The method of treating the retina may comprise an initial step of indentifying a region of the retina for treatment. This would be performed by imaging the retina.

The method of treating the retina may include obtaining an image of the retina at any point of the treatment process.

The method of treating the retina may comprise the further step of specifying the size and/or location of a treatment area.

The method of treating the retina may comprise the further step of controlling the operation of the plurality of light sources to select the area of the retina which is illuminated by the collimated light.

The method of treating the retina may comprise the further step of viewing an image of the retina. This may be performed at any point during the treatment process.

Embodiments of the present invention will now be described, by way of example only, with reference to the accompanying drawings, in which:—

Figure 1:
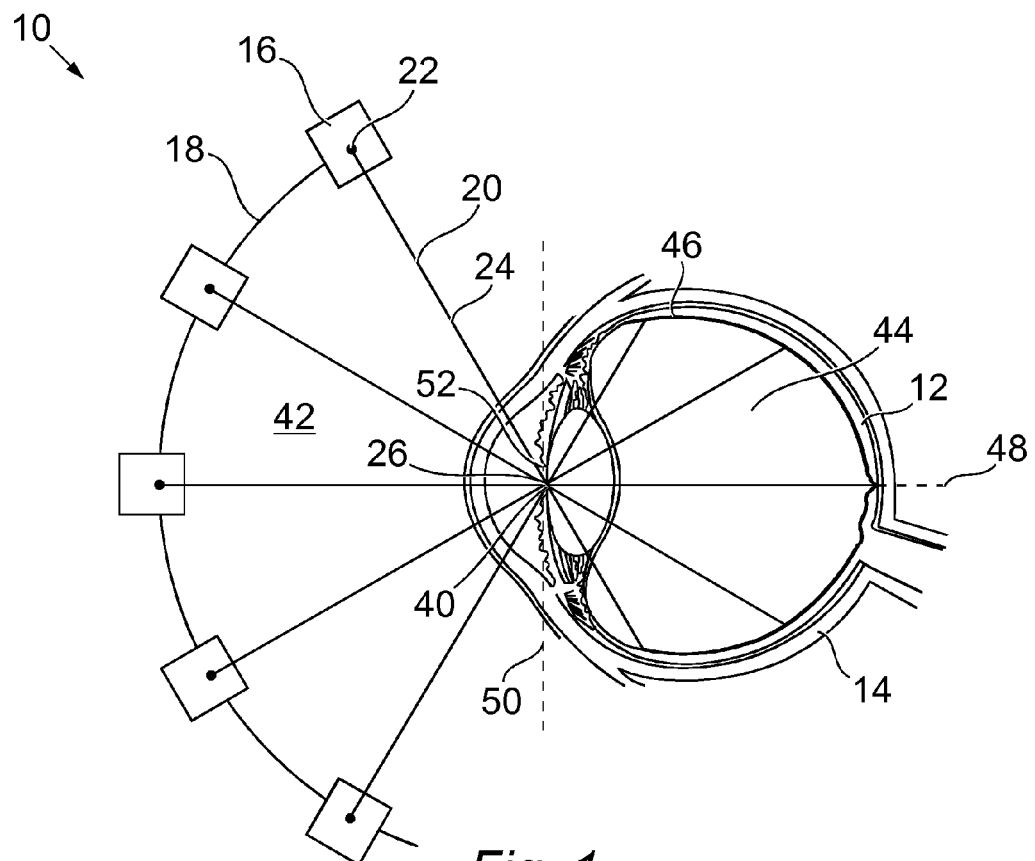
FIG. 1 is a schematic side view of an apparatus for illuminating, imaging and treating the retina of an eye according to the present invention.

FIG. 1 illustrates an apparatus 10 for illuminating the retina 12 of an eye 14. The apparatus 10 includes a plurality of light sources 16 arranged in an arc 18. Each light source 16 is adapted to provide collimated light 20 from a point source 22 and to direct the collimated light 20 from the point source 22 along the radius 24 of the arc 18 towards a centre point 26 of the arc 18.

The apparatus 10 may comprise between 100 and 16,000,000 light sources 16 arranged along the arc 18. However, it should be appreciated that the apparatus 10 may have less than 100 or more than 16,000,000 light sources 16. The apparatus 10 may also include any number of light sources 16 between 100 and 16,000,000 depending on the operating requirements of the apparatus 10.

The light sources 16 may be mounted to a frame (not shown), or the like. The frame may be in the shape of the arc 18.

The radius of the arc 18 may be between 3 mm and 500 mm. Preferably, the radius of the arc 18 may be between 5 mm and 200 mm. More preferably, the radius of the arc is 25 mm. However, is should be appreciated that the radius of the arc may be less than 3 mm or greater than 500 mm.

Each light source 16 may include a laser, light emitting diode (LED), Vertical Cavity Surface Emitting Laser (VCSEL), super luminescent diode, diode laser or a collimated incandescent lamp. Each light source 16 may also be adapted to provide light at a wavelength between 450 nm and 1000 nm. Preferably, each light source may be adapted to provide light at a wavelength between 488 nm and 700 nm. More preferably, each light source provides light at a wavelength between 515 nm and 650 nm. Each light source 16 may also be adapted to provide light at a power of between 500 nW and 1 W.

The wavelength of collimated light 20 of each light source 16 may be variable. Similarly, the power of each light source 16 may be variable. Each light source 16 may also includes a power monitor (see below) to ensure that the collimated light 20 provided by the light source 16 is safe.

Figure 2:
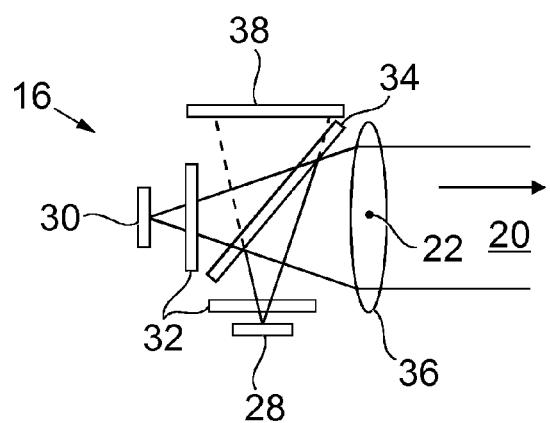
FIG. 2 is a schematic view of a light source and detector of FIG. 1.

The construction of each light source 16 is illustrated in FIG. 2. The light source 16 includes an emitter 28, which may include any one of the laser, light emitting diode (LED), Vertical Cavity Surface Emitting Laser (VCSEL), super luminescent diode, diode laser or a collimated incandescent lamp described above, and a detector 30. The detector 30 detects light reflected from the retina 12 and is used to form an image of the retina 12. The detector 30 may include a fast photo detector, such as an avalanche photo diode (APD), a PIN diode, a photomultiplier tube (PMT), a silicon photo multiplier (SPM), or a similar single point detector. Each detector 30 is a point detector.

Light from the emitter 28 is polarised by a polarising element 32 and directed towards a beam splitter 34. A portion of the light is reflected by the beam splitter 34 towards a collimating lens 36, with the remainder being transmitted towards a power monitor 38. The beam splitter 34 is a plate glass beam splitter and is oriented at 45 degrees to the collimating lens 36. The beam splitter 34 may be uncoated and provides approximately 90/10 splitting ratio by utilising polarisation specific Fresnel reflections. Approximately 90% of the light from the emitter 28 is transmitted through the beam splitter 34, with the remaining 10% going towards the collimating lens 36. The light transmitted through the beam splitter 34 may be used to monitor the power of the light for safety reasons. The collimating lens 36 collimates the light from the emitter 28 to provide the collimated light 20. The result is that the light source 16 provides collimated light 20 from a point source 22. With reference to FIGS. 1 and 2, the point source 22 is coincident with the collimating lens 36.

The apparatus 10 may be configured such that each light source 16 is independently operable. Furthermore, each light source 16 may be operated sequentially. The operation of each light source 16 may be automated and controlled by a computer, or the like.

The majority of the reflected light from the retina 12 is focussed by the collimating lens 36 to the detector 30. As described above, the detector 30 is a point detector. The reflected light from the retina 12 is transmitted through the beam splitter 34 to the detector 30 via another polarising element 32. As described above, the detector 30 may include a fast photo detector, such as an avalanche photo diode (APD), a PIN diode, a photomultiplier tube (PMT), a silicon photo multiplier (SPM), or a similar single point detector.

With reference to FIG. 1, in use, the apparatus 10 is arranged such that the centre point 26 of the arc 18 is substantially coincident with the pupillary point 40 of the eye 14. In this arrangement collimated light 20 from each of the light sources 16 is transmitted from each of the point sources 22 through the pupillary point 40 of the eye 14 to illuminate the retina 12. Reflected light from the retina 12 is detected by each detector 30 and an image of the retina 12 is obtained. In this arrangement the apparatus 10 illuminates the retina 12 and obtains an image of the illuminated part of the retina 12.

As illustrated in FIG. 1, the arrangement of the light sources 16 and the centre point 26 of the arc 18 define a plane 42. Since the collimated light 20 from each light source 16 is transmitted along this plane 42, the apparatus 10 may be considered as providing a plane of collimated light 44. Furthermore, since the collimated light 20 from each light source 16 is transmitted through the pupillary point 40 of the eye 14, the plane of collimated light 44 extends into the eye 14 and illuminates the retina 12.

The result of this is that the apparatus 10 illuminates and images a one-dimensional line 46 on the retina 12. In the embodiment illustrated in FIG. 1, the apparatus 10 is arranged such that the line 46 which is being illuminated is orthogonal to the optical axis 48 of the eye 14, i.e. a vertical line.

In order to facilitate two-dimensional illumination and imaging of the retina 12, the apparatus 10 may be rotatable about an axis 50 which lies on the plane 42. The axis 50 may be coincident with the pupillary point 40 of the eye 14. Locating the axis 50 at the pupillary point 40 of the eye 14 avoids clipping of the plane of collimated light 44 at the iris 52 as the light enters the eye 14. This ensures the widest field of illumination of light on the retina 12. Alternatively, the axis 50 may be located around the pupillary point 40 of the eye 14.

As described above, the light sources 16 may be mounted to a frame (not shown), or the like, in the shape of the arc 18. In this arrangement, the frame is adapted to be rotatable about the axis 50.

In this arrangement the apparatus 10 may be used to illuminate and image the surface of the retina 12 by rotating the apparatus 10 about the axis 50. It is important to note that, while the apparatus 10 is being rotated about the axis 50, each light source 16 directs the collimated light 20 towards the centre point 26 of the arc 18 and into the eye 14 in the same manner as described above. As the apparatus 10 is rotated about the axis 50 a plurality of one-dimensional lines 46 are illuminated and imaged. These line images are then combined to obtain a two-dimensional image of the retina 12. Thus, the surface of the retina 12 is illuminated and imaged by the apparatus 10.

The apparatus 10 also includes one or more data processing devices (not shown) for displaying and storing the images obtained. The one or more data processing devices may include one or more computers. The data processing devices are also configured to control the operation of the light sources 16 and the detectors 30. In particular, the data processing devices may be configured to sequentially operate each light source 16. That is, each light source 16 may be operated independently and in sequence to illuminate the retina 12. However, it should be appreciated that this sequential operation of each light source 16 is optional and the operation of the light sources 16 may be modified to suit a particular operational requirement of the apparatus 10.

The one or more data processing devices may also be configured to control the rotation of the apparatus 10 about the axis 50.

The apparatus 10 may be pivotable between a first position, in which the apparatus 10 may be used to illuminate the first retina 12 of a first eye 14, and a second position, in which the apparatus 10 may be used to illuminate a the second retina (not shown) of a second eye (not shown). The apparatus 10 can therefore illuminate and image both eyes of a patient.

Figure 3:
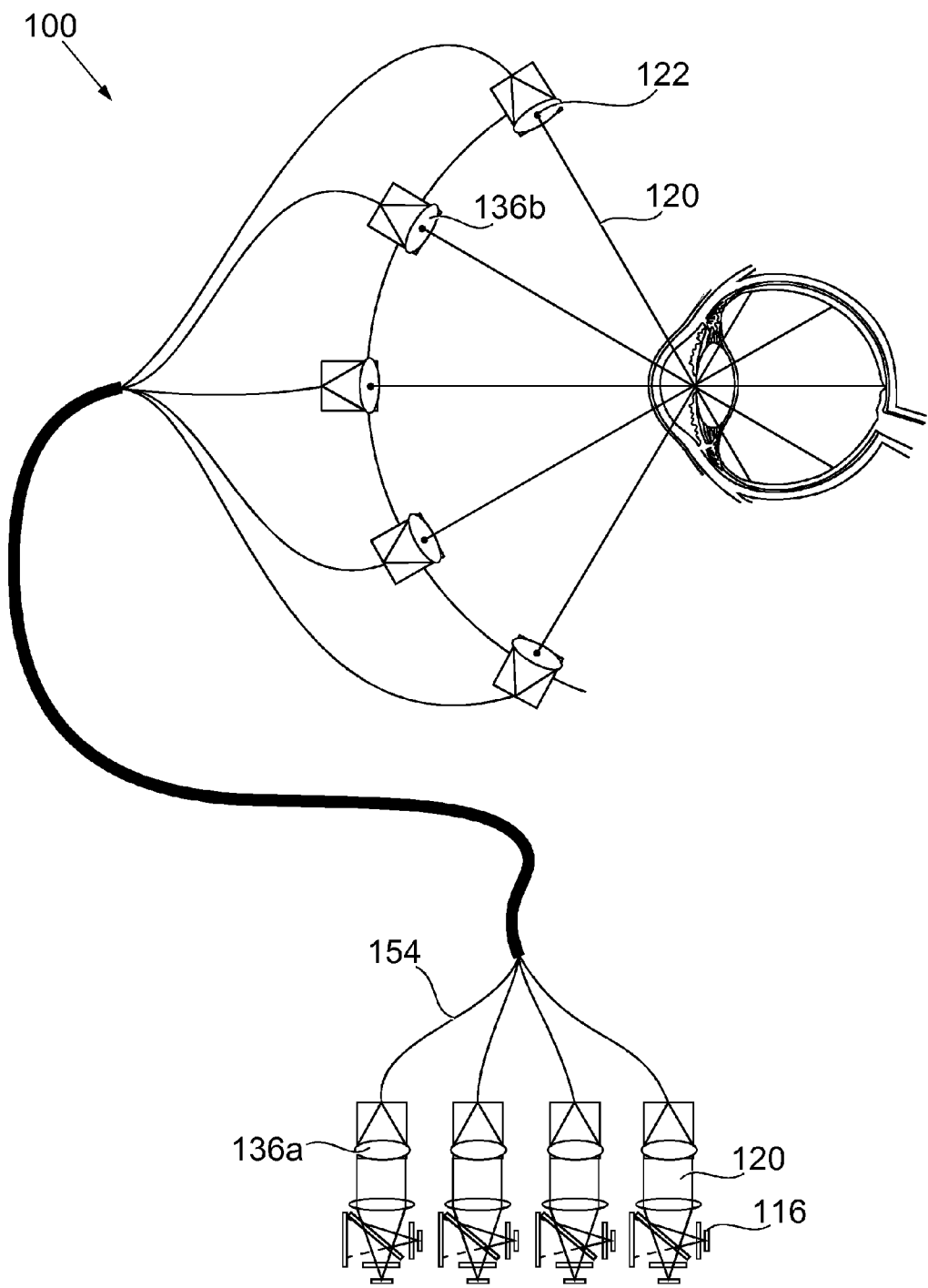
FIG. 3 is a schematic side view of an alternative apparatus for illuminating, imaging and treating the retina of an eye.

FIG. 3 illustrates an alternative embodiment of the apparatus 10. The arrangement and operation of the apparatus 100 of FIG. 3 is essentially identical to the apparatus 10 of FIG. 1, the only difference being that the light sources 116 are located remotely from the point source 122. As illustrated in FIG. 3, each light source 116 includes an additional collimating lens 136a which focuses the collimated light 20 to the input of an optical fibre 154 (an example of a light transfer device). Light from each light source 116 is transferred through the optical fibres 154 to a further collimating lens 136b which provides the collimated light 120 from the point source 122. The arrangement and operation of the light sources 116 is identical to the light sources 16 described above. The apparatus 100 operates in the same manner as the apparatus 10 to illuminate and image the retina 12 of the eye 14. Locating the light sources 116 remotely from the arc 18 simplifies the construction of the apparatus 100, reduces the size of the apparatus 100 and allows the use of larger collimated light sources, which can be housed separately. With this arrangement it is also possible to achieve a high density of input of collimated light without the physical restriction incurred by the source(s) themselves.

The apparatus 10, 100 of the present invention can be manufactured at a lower cost than known retinal illuminating and imaging apparatuses, such as scanning laser ophthalmoscopes (SLOs), as the apparatus 10, 100 does not require conventional laser scanning elements, such as polygon mirrors. The apparatus 10, 100 can be made more compact than known retinal imaging apparatuses, since the apparatus uses a smaller number of components than known retinal imaging apparatuses. The apparatus 10, 100 of the present invention also includes a smaller number of optical surfaces, which increases the optical efficiency of the apparatus. The result of this is that total power at the imaging detector is higher than known methods. Also, the apparatus 10, 100 may be capable of performing "wide field" illumination and imaging or "narrow field" illumination and imaging. Therefore, the apparatus 10, 100 is scalable for different markets.

Modifications and improvements may be made to the above without departing from the scope of the present invention. For example, it should be appreciated that the apparatus 10, 100 may also be used for fluorescence imaging by imaging at one wavelength and detecting at another, as is common in applications such as angiography and auotofluorescence imaging. It should therefore be appreciated that the apparatus 10, 100 may obtain an image of the retina by receiving light reflected from the retina or fluorescent light emitted by the retina on excitation thereof. Also, the apparatus 10, 100 may use a combination of reflection and fluorescence imaging and treatment.

Furthermore, although the emitter 28 and detector 30 have been illustrated and described above as operating with a single collimating lens 36, it should be appreciated that the emitter 28 and detector 30 may have independent lenses, with a beam splitter, or the like, positioned after the lenses to combine them into a single optical path.

Also, although the plurality of light sources 16 have been illustrated and described above as being arranged on an arc 18 having a radius 24, it should be appreciated that the arc 18 does not necessarily have to be circular. The plurality of light sources 16 may be arranged in any suitable shape, so long as the collimated light from the point source 22 is directed towards a centre point of the shape, and that, in use, the centre point of this shape is coincident with the pupillary point 40 of the eye 14. For example, the arc 18 could be elliptical, or any other suitable non-circular shape.

Furthermore, although each light source 16, 116 has been illustrated and described above as comprising a single emitter 28, it should be appreciated that each light source 16, 116 may include one or more emitters of differing wavelengths.

Also, although the centre of the arc 18 has been illustrated and described above as being coincident with the pupillary point 40 of the eye 14, it should be appreciated that the centre of the arc 18 could be located generally around the pupillary point 40 of the eye 14.

Furthermore, although the apparatus 10, 100 has been illustrated and described above as comprising a single arc of light sources 16, 116, and that the apparatus 10, 100 is rotated about the axis 50 to illuminate and image the surface of the retina 12, it should be appreciated that in an alternate embodiment of the present invention, the apparatus 10, 100 may comprise a plurality of collimated point sources lying on a plurality of concentrically aligned arcs. In this arrangement collimated light from each point source is directed radially inwardly along the radius of each arc towards the centre point. In use, the apparatus 10, 100 is arranged such that the centre point of each arc is substantially coincident with the pupillary point of the eye, such that collimated light is transmitted from each point source on each arc through the pupillary point of the eye to illuminate the retina. The apparatus 10, 100 in this form takes the shape of a two-dimensional semi-spherical illuminating and detecting surface for directing collimated light from each point source through the centre point and to the retina, and detecting the reflected light.

Also, although the apparatus 10, 100 has been described above as for illuminating and imaging the retina 12 of the eye 14, it should be appreciated that the apparatus 10, 100 may also be used to administer treatment to the retina 12 by illuminating the retina 12 with collimated light of a suitable wavelength and/or power. Treating the retina 12 may include the following steps: (i) identifying a region of the retina for treatment, (ii) specifying the size of the treatment area through treatment planning, linked to an imaging system and (iii) guiding the treatment either through manual control or pre-specified automated control to deliver the treatment illumination to single or multiple sites via a common input path to the imaging source(s). This provides a correlation between the treatment geography and treatment planning derived from the imaging system. Treating the retina 12 may also include the optional steps of viewing an image of the retina 12 during the treatment and/or re-imaging the retina to confirm the treatment is successful.

That is, the present invention also provides an apparatus for illuminating the retina with collimated light for use in treating the retina. The present invention also provides a method for illuminating the retina with collimated light for use in treating the retina.

Furthermore, although in the embodiments illustrated and described above the apparatus 10, 100 includes a plurality of light sources 16, 116, with each light source 16, 116 providing collimated light from a point source 22, 122, it should be appreciated that the apparatus 10, 100 may only include a single light source, and that this single light source could provide collimated light to the plurality of point sources 22, 122. In this arrangement the collimated light from the single light source could be split into a number of channels which provide the collimated light to point sources.

The invention claimed is:

1. An apparatus for imaging the retina of an eye comprising:
    at least one light source adapted to provide collimated light from a plurality of origin points,
    and wherein collimated light from each origin point is directed radially towards a centre point, the origin points and the centre point lying in a single plane, the collimated light from each origin point provided by a respective collimating lens associated with the origin point,
    a plurality of light detectors, each light detector being associated with one origin point and the respective collimating lens associated with the origin point and being adapted to detect light originating from its associated origin point and reflected from the retina at a point in said plane, the light reflected from the retina passing through the collimating lens associated with the light detector towards the light detector,
    and wherein the apparatus is adapted such that the centre point is arranged substantially coincident with the pupillary point of the eye, such that collimated light is transmitted from each origin point along an optical path between the origin point and the pupillary point through the pupillary point of the eye to illuminate the retina and reflected back, along at least a portion of the same respective optical path between the pupillary point and the origin point, to the respective light detector associated with the respective origin point to produce an image of the retina.

2. An apparatus according to claim 1, wherein the apparatus comprises a plurality of light sources, wherein each light source is adapted to provide collimated light from each origin point.

3. An apparatus according to claim 2, wherein each light source includes one or more light sources of differing wavelengths.

4. An apparatus according to claim 2, wherein each light source is configured such that the wavelengths of light provided is variable.

5. An apparatus according to claim 2, wherein each light source is configured such that the power of light provided is variable.

6. An apparatus according to claim 2, wherein each light source is positioned at or adjacent the origin point.

7. An apparatus according to claim 2, wherein each light source is positioned remotely from the origin point and light is transferred from each light source to the origin point via a light transfer device.

8. An apparatus according to claim 2, wherein each light source is independently operable.

9. An apparatus according to claim 1, wherein the plurality of origin points lie on an arc of radius between 3 mm and 500 mm.

10. An apparatus according to claim 1, wherein the apparatus is rotatable about an axis which substantially lies on said single plane defined by the plurality of origin points and the centre point.

11. An apparatus according to claim 1, wherein the light detectors detect light over an angle around the centre point that is as great as an angle spanned by the origin points around the center point.

12. An apparatus according to claim 11, wherein respective said light detectors detect light at the positions of respective said origin points.

13. A method of imaging the retina of an eye comprising the steps of:
providing at least one light source, wherein the at least one light source is adapted to provide collimated light from a plurality or origin points, the collimated light from each origin point provided by a respective collimating lens associated with the origin point;
arranging the apparatus such that a centre point is substantially coincident with the pupillary point of the eye, wherein the origin points and the centre point lie on a single plane; and
using the at least one light source to direct collimated light from each origin point radially towards the centre point, such that collimated light is transmitted from the origin point along an optical path between the origin point and the pupillary point through the pupillary point of the eye to illuminate the retina; and
providing a plurality of light detectors, each light detector being associated with one origin point and the respective collimating lens associated with the origin point, and using each light detector to detect light originating from its associated origin point and reflected from the retina back, along at least a portion of the same respective optical path between the origin point and the pupillary point, to the respective light detector associated with the origin point to produce an image of the retina, the light reflected from the retina passing through the collimating lens associated with the light detector towards the light detector.

14. A method according to claim 13, wherein the apparatus comprises a plurality of light sources, wherein each light source is adapted to provide collimated light from each origin point.

15. A method according to claim 14, wherein each light source is configured such that the wavelength of light provided is variable and the method includes the further step of varying the wavelength of light from the source.

16. A method according to claim 14, wherein each light source is configured such that the power of light provided is variable and the method includes the further step of varying the power of light from the source.

17. A method according to claim 14, wherein each light source is independently operable and the method includes the further step of operating each light source sequentially.

18. A method according to claim 14, wherein the apparatus is rotatable about an axis which substantially lies on said single plane and the method includes the further step of rotating the apparatus about the axis to illuminate the surface of the retina.

19. A method according to claim 13, comprising using the light detectors to detect the light over an angle around the centre point that is as great as an angle spanned by the origin points around the center point.

20. A method according to claim 19, comprising providing respective said light detectors to detect light at the positions of respective said origin points.

* * * * *